US00PP24899P2

(12) United States Plant Patent
Leue

(10) Patent No.: US PP24,899 P2
(45) Date of Patent: Sep. 16, 2014

(54) *HEUCHERA* PLANT NAMED 'CARNIVAL LIMEADE'

(50) Latin Name: *Heuchera×hybrida*
Varietal Denomination: Carnival Limeade

(75) Inventor: Ellen Leue, Dekalb, IL (US)

(73) Assignee: Ball Horticultural Company, West Chicago, IL (US)

( * ) Notice: Subject to any disclaimer, the term of this patent is extended or adjusted under 35 U.S.C. 154(b) by 284 days.

(21) Appl. No.: 13/507,885

(22) Filed: Aug. 3, 2012

(51) Int. Cl.
*A01H 5/00* (2006.01)

(52) U.S. Cl.
USPC ..... Plt./440

(58) Field of Classification Search
CPC ..... A01H 5/02; A01H 5/12; A01H 5/00
USPC ..... Plt./440
See application file for complete search history.

*Primary Examiner* — June Hwu
(74) *Attorney, Agent, or Firm* — Audrey Charles

(57) ABSTRACT

A new and distinct cultivar of *Heuchera* plant named 'Carnival Limeade', characterized by its lime-green and silver colored foliage, pink-colored flowers, and moderately vigorous, mounded growth habit, is disclosed.

1 Drawing Sheet

Latin name of genus and species of plant claimed: *Heuchera×hybrida.*

Variety denomination: 'Carnival Limeade'.

BACKGROUND OF THE INVENTION

The present invention relates to a new and distinct cultivar of *Heuchera* plant botanically known as *Heuchera×hybrida* and hereinafter referred to by the cultivar name 'Carnival Limeade'.

The new cultivar originated in a controlled breeding program in Elburn, Ill. during April 2008. The objective of the breeding program was the development of *Heuchera* cultivars with unique foliage coloration and mounded growth habit.

The new *Heuchera* cultivar is the result of cross-pollination. The female (seed) parent of the new cultivar is 'Lime Rickey', U.S. Plant Pat. No. 16,210, characterized by its lime-green colored foliage, white-colored flowers, and vigorous, mounded growth habit. The male (pollen) parent of the new cultivar is the proprietary *Heuchera×hybrida* breeding selection coded 228-3, not patented, characterized by its light brownish-green and silver colored foliage, light red-colored flowers, and vigorous, mounded growth habit. The new cultivar was discovered and selected as a single flowering plant within the progeny of the above stated cross-pollination during April 2010 in a controlled environment in Elburn, Ill.

Asexual reproduction of the new cultivar by in vitro propagation since April 2010 in West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Carnival Limeade' as a new and distinct cultivar of *Heuchera* plant:

1. Lime-green and silver colored foliage;
2. Pink-colored flowers; and
3. Moderately vigorous, mounded growth habit.

Plants of the new cultivar differ from plants of the male parent primarily in having a different foliage color and reduce growth vigor.

Of the many commercially available *Heuchera* cultivars, the most similar in comparison to the new cultivar is the female parent 'Lime Rickey', U.S. Plant Pat. No. 16,210. However, in comparison, plants of the new cultivar differ from plants of 'Lime Rickey' in at least the following characteristics:

1. Plants of the new cultivar have lime-green with silver colored foliage unlike plants of 'Lime Rickey';
2. Plants of the new cultivar have a foliage margin that is less wavy than plants of 'Lime Rickey'; and
3. Plants of the new cultivar have a flower color different from plants of 'Lime Rickey'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Carnival Limeade'. The plants were grown in one-gallon containers for approximately one year in a greenhouse in West Chicago, Ill.

DETAILED BOTANICAL DESCRIPTION

Figure 1:
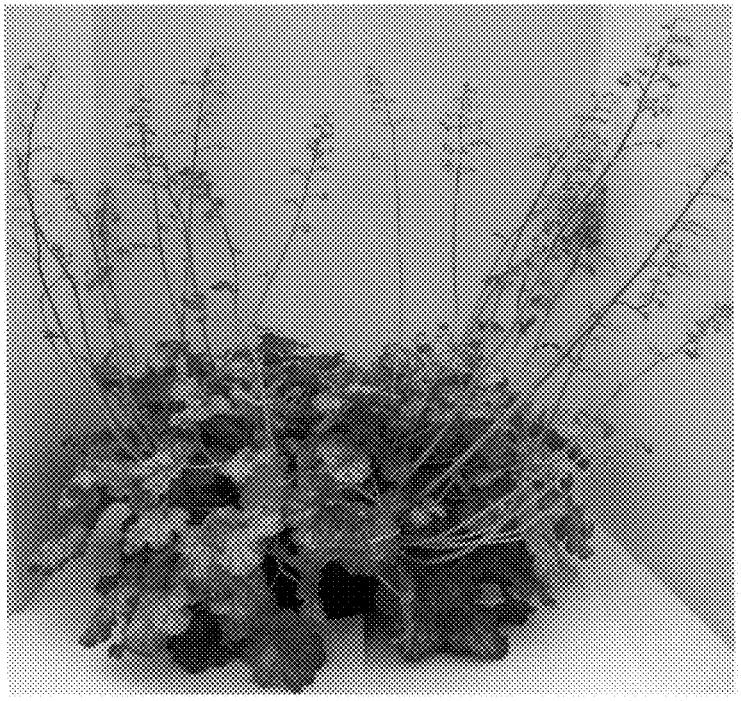
FIG. 1 illustrates a side view of the overall growth habit of 'Carnival Limeade'.
Figure 2:
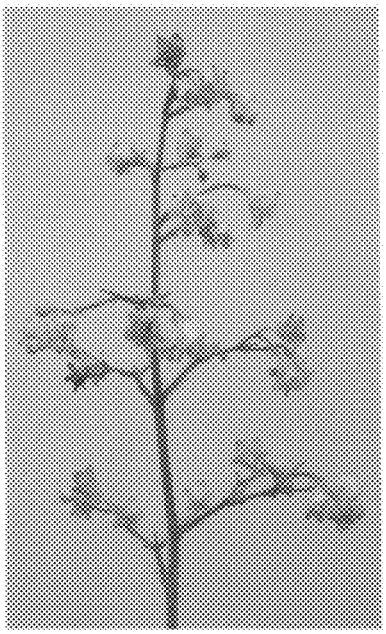
FIG. 2 illustrates a close-up view of an individual inflorescence of 'Carnival Limeade'.
Figure 3:
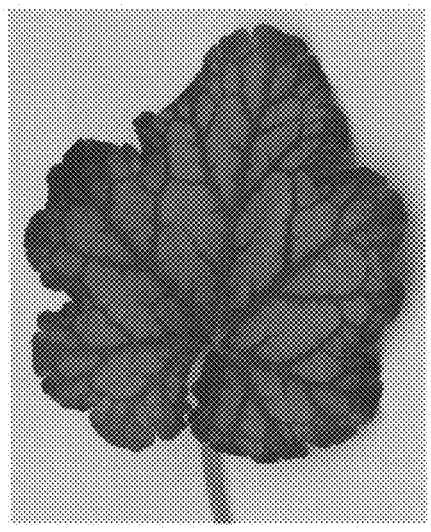
FIG. 3 illustrates a close-up view of an individual leaf of 'Carnival Limeade'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in May 2012 under natural light conditions in West Chicago, Ill.

The following descriptions and measurements describe plants produced from in vitro plantlets and grown in a glass-covered greenhouse under conditions comparable to those used in commercial practice. The plants were grown in West Chicago, Ill. in one-gallon containers for approximately one year utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Heuchera×hybrida* cultivar Carnival Limeade.

Parentage:

*Female parent*.—'Lime Rickey', U.S. Plant Pat. No. 16,210.

*Male parent*.—Proprietary *Heuchera×hybrida* breeding selection coded 228-3, not patented.

Propagation:

*Type*.—In vitro propagation is preferred, divisions are possible.

*Time to initiate roots in vitro*.—Approximately 10 days at 20° C.

*Time to initiate roots in greenhouse*.—Approximately 20 days at 20° C.

*Time to produce a rooted plantlet in summer*.—Approximately 42 days.

*Root description*.—Fine, fibrous; white to ivory m color.

*Rooting habit*.—Freely branching.

Plant description:

*Commercial crop time*.—Approximately 20 weeks from a rooted tissue culture plantlet to finish in a 1 gallon container.

*Growth habit and general appearance*.—Clump-forming herbaceous perennial, mounded foliage.

*Growth rate*.—Moderately vigorous.

*Outdoor plant performance*.—Use as bedding plants or in mixed-container plantings; at least tolerant to temperatures up to 35° C. and hardy to USDA zone 3.

*Size*.—Height from soil level to top of plant plane: Approximately 55.5 cm. Height from soil level to top of foliage: Approximately 19.0 cm. Width: Approximately 62.0 cm.

*Branching habit*.—No branching, basal rosettes of leaves on petioles. Number of rosettes per plant: Approximately 11.

Foliage description:

*General description*.—Moderately durable to environmental stresses. Quantity of leaves per rosette: Approximately 10. Fragrance: None. Form: Simple. Arrangement: Alternate.

*Leaves*.—Aspect: Blade is nearly perpendicular to petiole. Shape: Orbicular. Margin: Crenate, shallowly lobed, slightly wavy. Apex: Broadly acute. Base: Cordate, sometimes moderately overlapping. Venation pattern: Palmate. Length of mature leaf: Approximately 9.5 cm. Width of mature leaf: Approximately 9.5 cm. Texture of upper surface: Dull, slightly rough, sparsely pubescent with short hairs. Texture of lower surface: Slightly glossy, moderately pubescent with short hairs. Color of upper surface of young foliage: 192C with venation area and margins of 137C. Color of lower surface of young foliage: Closest to 147D with venation of 145D. Color of upper surface of mature foliage: 192C with venation area and margins of 144B. Color of lower surface of mature foliage: Closest to 145C with venation of 145D.

*Petiole*.—Length: Approximately 18.0 cm. Diameter: Approximately 3.0 mm. Texture: Densely pubescent. Color: 145B to 145C.

*Stipules*.—Two leafy stipules located at the base of each petiole. Apex: Narrow acute. Length: Approximately 2.0 cm. Width: Approximately 4.0 mm. Color: 145D.

Flowering description:

*Flowering habit*.—'Carnival Lemonade' flowers once a year during late spring to midsummer under outdoor conditions.

*Lastingness of individual flower on the plant*.—Approximately 7 days.

Inflorescence description:

*General description*.—Type: Compound spike emerging from the base of the rosette with one to two cauline leaves. Fragrance: None. Length or height excluding the peduncle: Approximately 20.0 cm. Width: Approximately 7.0 cm. Quantity of inflorescences per plant: Approximately 24. Quantity of flowers per inflorescence: Approximately 80.

*Peduncle*.—Strength: Moderate. Aspect: Erect to approximately 45° angle from vertical. Length: Approximately 30.0 cm. Diameter at midpoint: Approximately 3.0 to 4.0 mm. Texture: Densely pubescent. Color: 145B occasionally with an overlay of 181B near inflorescence.

Flower description:

*General description*.—Type: Single, campanulate, self-cleaning. Aspect: Drooping to slightly outward.

*Bud*.—Rate of opening: Generally takes 4 days for bud to progress from first color to fully open flower.

*Bud just before opening*.—Shape: Broadly obovate. Length: Approximately 4.0 mm. Diameter: Approximately 3.0 mm. Texture: Densely glandular pubescent. Gland Color: 55A. Color: 144C with base of 54D.

*Corolla*.—Shape: Campanulate. Diameter: Approximately 6.0 mm. Depth: Approximately 7.0 mm.

*Petals*.—Quantity: 5. Arrangement: Single whorl. Shape: Narrowly elliptic. Appearance: Dull. Margin: Entire. Apex: Acute. Base: Lower half fused into hypanthium. Length: Approximately 7.0 mm. Width: Approximately 2.0 mm. Texture of upper and lower surfaces: Densely pubescent with a mixture of glandular and nonglandular hairs. Gland color: Colorless, transparent. Color of upper and lower surfaces when first open: 55C. Color of upper and lower surfaces when fully open: 55D.

*Calyx*.—Shape: Campanulate. Diameter: Approximately 6.0 mm. Depth: Approximately 7.0 mm.

*Sepals*.—Quantity per flower: 5. Shape: Obovate. Appearance: Dull. Margin of free portion: Entire. Apex: Broadly acute. Base: Lower half fused into hypanthium. Length: Approximately 7.0 mm. Width at rim of hypanthium: Approximately 3.0 mm. Texture of upper and lower surfaces: Densely pubescent with a mixture of glandular and nonglandular hairs. Gland color: Mixture of 55A and colorless, transparent. Color of upper and lower surfaces: 55B fading to 55D with age.

*Pedicel*.—Strength: Moderate. Aspect: The pedicel of the central flower of each spikelet is directly on top of the secondary pedicel, pedicels of secondary and tertiary flowers of each spikelet have an average 40° angle from vertical. Length: Approximately 4.0 mm. Diameter: Less than 1.0 mm. Texture: Densely glandular pubescent. Gland color: 55A and colorless, transparent. Color: 145B occasionally with an overlay of 181B.

*Reproductive organs*.—Androecium: Quantity: none observed. Gynoecium: Pistil quantity: 10 to 20 per flower. Pistil length: Approximately 4.0 mm for main 10 pistils with additional deformed pistils of 2.0 to 3.0 mm. Stigma shape: Pointed. Stigma color: 157D. Style length: Approximately 2.0 mm. Style color: 61B to 61C. Ovary color: 144D.

Seed and fruit production: Neither seed nor fruit production has been observed.

Disease and pest resistance: Resistance to pathogens and pests common to *Heuchera* has not been observed.

What is claimed is:

1. A new and distinct cultivar of *Heuchera* plant named 'Carnival Limeade', substantially as herein shown and described.

* * * * *